(12) United States Patent
Chintamaneni et al.

(10) Patent No.: US 11,049,594 B2
(45) Date of Patent: Jun. 29, 2021

(54) COMPUTER-IMPLEMENTED SYSTEM AND METHOD OF FACILITATING ARTIFICIAL INTELLIGENCE BASED REVENUE CYCLE MANAGEMENT IN HEALTHCARE

(71) Applicant: RevvPro Inc., Somerset, NJ (US)

(72) Inventors: Sai Giridhar Chintamaneni, Hyderabad (IN); Chirag Bhai Patel, Hyderabad (IN)

(73) Assignee: RevvPro Inc., Somerset, NJ (US)

( * ) Notice: Subject to any disclaimer, the term of this patent is extended or adjusted under 35 U.S.C. 154(b) by 109 days.

(21) Appl. No.: 15/991,301

(22) Filed: May 29, 2018

(65) Prior Publication Data
US 2019/0371438 A1 Dec. 5, 2019

(51) Int. Cl.
| | |
|---|---|
| *G16H 10/60* | (2018.01) |
| *G06Q 10/10* | (2012.01) |
| *G06N 5/02* | (2006.01) |
| *G06Q 40/08* | (2012.01) |
| *G06N 20/00* | (2019.01) |
| *G10L 15/26* | (2006.01) |
| *G16H 15/00* | (2018.01) |
| *G10L 15/00* | (2013.01) |

(52) U.S. Cl.
CPC ............ *G16H 10/60* (2018.01); *G06N 5/025* (2013.01); *G06N 20/00* (2019.01); *G06Q 10/10* (2013.01); *G06Q 40/08* (2013.01); *G10L 15/00* (2013.01); *G10L 15/26* (2013.01); *G16H 15/00* (2018.01)

(58) Field of Classification Search
CPC ........ G16H 10/60; G16H 15/00; G10L 15/26; G10L 15/00; G06F 17/243; G06F 19/328
See application file for complete search history.

(56) References Cited

U.S. PATENT DOCUMENTS

| | | | | |
|---|---|---|---|---|
| 6,915,254 | B1 * | 7/2005 | Heinze | G06F 17/27 704/9 |
| 7,555,425 | B2 * | 6/2009 | Oon | G06F 17/2785 704/270 |
| 9,424,532 | B1 * | 8/2016 | Abedini | G16H 50/20 |
| 2003/0046006 | A1 * | 3/2003 | Eastwood | G01V 1/34 702/14 |
| 2003/0120632 | A1 * | 6/2003 | Casey | G06Q 10/10 |
| 2003/0135393 | A1 * | 7/2003 | Burgess | G16H 15/00 705/3 |

(Continued)

*Primary Examiner* — Samuel G Neway
(74) *Attorney, Agent, or Firm* — Zilka-Kotab, P.C.

(57) ABSTRACT

A system and method of facilitating revenue cycle management in healthcare are disclosed. A voice module records a physician treating a patient. A speech to text engine converts the recorded voice into a text format to generate a transcription file. The rules are based on the outcome/learning of the artificial intelligence engine to processes the text to automatically populate data field(s) associated with the diagnosis and treatment in a transcription template. The artificial intelligence engine processes document(s) associated with the diagnosis and treatment of the patient to identify code(s) and populating coding field(s) with the code(s). The rules from the dynamic rules engine are used to processes data records associated with the patient to automatically populate field(s) in an insurance claim form of an insurance claim associated with the patient, and identify a payor to be billed with an appropriate amount determined based upon the code(s) identified.

10 Claims, 9 Drawing Sheets

(56) References Cited

U.S. PATENT DOCUMENTS

| | | | |
|---|---|---|---|
| 2003/0154085 A1* | 8/2003 | Kelley | G06F 17/243 704/275 |
| 2004/0220895 A1* | 11/2004 | Carus | G06Q 50/22 |
| 2006/0041487 A1* | 2/2006 | Santalo | G06Q 20/102 705/30 |
| 2006/0173679 A1* | 8/2006 | DelMonego | G06F 17/243 704/235 |
| 2006/0259325 A1* | 11/2006 | Patterson | G06Q 50/22 705/2 |
| 2007/0228146 A1* | 10/2007 | Rogers | G06Q 50/22 235/379 |
| 2008/0103833 A1* | 5/2008 | Miglietta | G06Q 10/10 705/3 |
| 2009/0157436 A1 | 6/2009 | Craycraft | |
| 2010/0114598 A1* | 5/2010 | Oez | G06Q 10/10 705/2 |
| 2011/0166875 A1* | 7/2011 | Hayter | G06Q 10/10 705/2 |
| 2012/0166212 A1* | 6/2012 | Campbell | G06Q 50/22 705/2 |
| 2013/0054259 A1* | 2/2013 | Wojtusiak | G06Q 10/10 705/2 |
| 2014/0006061 A1* | 1/2014 | Watanabe | G06Q 40/08 705/4 |
| 2014/0324448 A1* | 10/2014 | Lacy | G06Q 50/22 705/2 |
| 2015/0169827 A1* | 6/2015 | LaBorde | H04L 9/0861 705/51 |
| 2015/0317337 A1 | 11/2015 | Edgar | |
| 2016/0180030 A1 | 6/2016 | Gunawardena et al. | |
| 2018/0129900 A1* | 5/2018 | Kiraly | G16H 30/20 |
| 2018/0322249 A1* | 11/2018 | Allen | G16H 20/10 |
| 2018/0349327 A1* | 12/2018 | Yang | G06F 17/273 |
| 2019/0371438 A1* | 12/2019 | Chintamaneni | G10L 15/265 |

* cited by examiner

COMPUTER-IMPLEMENTED SYSTEM AND METHOD OF FACILITATING ARTIFICIAL INTELLIGENCE BASED REVENUE CYCLE MANAGEMENT IN HEALTHCARE

TECHNICAL FIELD

The present disclosure described herein, in general, relates to a revenue cycle management in healthcare, and more particularly, relates to a computer implemented system and method of revenue cycle management in healthcare using artificial intelligence and machine learning techniques.

BACKGROUND

In a typical revenue cycle management of healthcare systems facilitating insurance reimbursements, there exists phases including a transcription phase, a coding phase, a billing phase, a payment posting phase and a denial management phase. In the transcription phase, a doctor or physician dictates treatment or consultation provided to a patient wherein such dictation is recorded in the form of a transcription file also known as an Electronic Medical Record. Usually, the transcription file is manually generated by a transcriptionist who listens to and transcribes the dictation, resulting in a transcription that is prone to errors. The physician/doctor needs to manually rectify the errors in the transcription file before being finalized and sending to the coding phase. In the coding phase, a dedicated coder team is employed for analyzing the consultation, diagnosis and treatment provided by the doctor or physician to the patient based upon the contents in the transcription file. The analysis of the diagnosis and treatment is performed by the coder team to map one or more codes from an ICD (International classification of diseases) library storing a plurality of codes.

Since, the codes are mapped manually based upon the transcription file, there is a high probability of incorrect mapping of the one or more codes with the diagnosis not only due to the errors caused in the generation of the transcription file, but also, due to manual mapping of the codes from the ICD library by the coder team. The one or more codes mapped to an insurance master/fee schedule are used in the billing phase to determine an appropriate insurance amount to be paid to the doctor or physician by a payor (i.e. an insurer) on behalf of the patient (i.e. an insurer) and confirm the payment in the payment posting phase. Since the billing is based upon the one or more codes mapped from the ICD library, the incorrect mapping of the one or more codes results in determining an inappropriate insurance amount. In other words, the insurance claimed by the doctor/physician is either underpaid or overpaid which further results in denial of the insurance claim by the payor. The denial of insurance claim may further be due to errors in recording the diagnosis & treatment of the patient, and mapping of codes as-well-as in identifying the payor for payment to the doctor or physician.

Therefore, in a current scenario, various phases associated with the revenue cycle management including the transcription phase, the coding phase, the billing phase, and the payment posting phase are operated in different fragments and there is no interconnection between individual phases. Further, since human resources are employed for implementing various processes associated with the revenue cycle management, a substantial amount of time is wasted in rectifying errors generated at various stages of the revenue cycle management thereby resulting in overall increase in time of the revenue cycle. Further, the probability of insurance claims being denied and/or underpaid/overpaid is increased due to presence of the errors not being rectified.

SUMMARY

This summary is provided to introduce aspects related to computer implemented systems and methods of facilitating revenue cycle management in healthcare and are further described below in the detailed description. This summary is not intended to identify essential features of the subject matter nor is it intended for use in determining or limiting the scope of the subject matter.

In one embodiment, a computer implemented system of facilitating revenue cycle management (RCM) in healthcare is disclosed. The system may include a processor and a memory coupled with the processor. The processor may execute a plurality of modules stored in the memory. The plurality of modules may include a voice recording module, a speech to text engine, dynamic rules engine, an artificial intelligence engine and an interactive dashboard module. The processor may execute the voice recording module for recording a voice of a physician treating a patient, wherein the voice recorded is associated with a diagnosis and treatment for the patient. The processor may further execute a speech to text engine for converting the voice recorded into a text format to generate a transcription file. Further, the processor may execute rules from the dynamic rules engine which sets the rules based on the outcome/learning of the artificial intelligence for processing the text in the transcription file to automatically populate one or more data fields associated with the diagnosis and treatment in a transcription template selected from a plurality of predefined templates. The processor may further execute the artificial intelligence engine for processing one or more documents associated with the diagnosis and treatment of the patient to identify the diagnosis and provide clinical decision support where needed. Further, the processor may further execute the artificial engine for processing the one or more documents to also provide one or more codes from a plurality of codes pre-stored in the memory and populating one or more coding fields with the said one or more codes. Further, the processor may execute the rules from the dynamic rules engine which sets the rules based on the outcome/learning of the artificial intelligence engine for processing data records associated with the patient to automatically populate one or more fields in an insurance claim form of an insurance claim associated with the patient and identify a payor to be billed with an appropriate amount determined based upon the one or more codes identified. In accordance with an aspect of this embodiment, the processor may further execute the rules from the dynamic rules engine which sets the rules based on the outcome/learning of the artificial intelligence engine to compare explanation of benefits (EOB) associated with the insurance claim with a predefined master file to detect the insurance claim being underpaid, overpaid, or denied. The insurance claim being detected as underpaid, overpaid, or denied is further re-assessed by the artificial intelligence engine to correct the deficiencies associated with the insurance claim and thereby re-billing the insurance claim. The system may further include a claim processing module stored in the memory to confirm and validate the processing of the insurance claim associated with the patient and posting the insurance claim for payment to the payor. Further, the system may include the interactive dashboard module to display, on a user device associated with the physician, the entire RCM workflow and a financial status, and further one or more of the transcription template populated with the one or more data fields, a charge entry form populated with the one or more codes to be submitted to a clearing house or the payor, and an indicative amount to be paid by the payor, wherein the indicative amount is populated and displayed based upon the data from the transcription template and the charge entry form. Furthermore, the system may include a machine learning module for continuously training the artificial intelligence engine based upon historical data associated with transcription, coding, billing, over-payment, under-payment, or denial of prior insurance claims.

In another embodiment, a computer implemented method of facilitating revenue cycle management (RCM) in healthcare is disclosed. The method may include recording, via a processor, a voice of a physician treating a patient, wherein the voice recorded is associated with a diagnosis and treatment for the patient. Further, the method may include converting, via the processor, the voice recorded into a text format to generate a transcription file. Further, the method may include processing, via the processor, the text in the transcription file to automatically populate one or more data fields associated with the diagnosis and treatment in a transcription template selected from a plurality of predefined templates. The method may further include processing, via the processor, one or more documents associated with the diagnosis and treatment of the patient to identify one or more codes from a plurality of codes pre-stored in a memory coupled with the processor and populating one or more coding fields with the said one or more codes. Further, the method may include processing, via the processor, data records associated with the patient to automatically populate one or more fields in an insurance claim form of an insurance claim associated with the patient and identify a payor to be billed with an appropriate amount determined based upon the one or more codes identified. In accordance with aspect of this embodiment, the method may further include comparing, via the processor, explanation of benefits (EOB) associated to the insurance claim with a predefined master file to detect the insurance claim being underpaid, overpaid, or denied. The insurance claim being detected as underpaid, overpaid, or denied may be further re-assessed by the artificial intelligence engine to correct the deficiencies associated with the insurance claim and thereby re-billing the insurance claim. The method may further include confirming and validating, via the processor, the processing of the insurance claim associated with the patient and posting the insurance claim for payment to the payor. The method may further include displaying, via the processor, on a user device associated with the physician, the entire RCM workflow and a financial status, and further one or more of the transcription template populated with the one or more data fields, a charge entry form populated with the one or more codes to be submitted to a clearing house or the payor, and an indicative amount to be paid by the payor, wherein the indicative amount is populated and displayed based upon the data from the transcription template and the charge entry form. Furthermore, the method may include continuously training the processor based upon historical data associated with transcription, coding, billing, over-payment, under-payment, or denial of prior insurance claims.

In yet another embodiment, non-transitory computer readable medium storing a program of facilitating revenue cycle management (RCM) in healthcare is disclosed. The program may include programmed instructions for recording a voice of a physician treating a patient, wherein the voice recorded is associated with a diagnosis and treatment for the patient. Further, the program may include programmed instructions for converting the voice recorded into a text format to generate a transcription file. Further, the program may include programmed instructions for processing the text in the transcription file to automatically populate one or more data fields associated with the diagnosis and treatment in a transcription template selected from a plurality of predefined templates. The program may further include programmed instructions for processing one or more documents associated with the diagnosis and treatment of the patient to identify one or more codes from a plurality of codes that are pre-stored in a memory and populating one or more coding fields with the said one or more codes. Further, the program may include programmed instructions for processing data records associated with the patient to automatically populate one or more fields in an insurance claim form of an insurance claim associated with the patient and identify a payor to be billed with an appropriate amount determined based upon the one or more codes identified. In accordance with an aspect of this embodiment, the program may further include programmed instructions for comparing explanation of benefits (EOB) associated with the insurance claim with a predefined master file to detect the insurance claim being underpaid, overpaid, or denied. The insurance claim being detected as underpaid, overpaid, or denied may be re-assessed by the artificial intelligence engine to correct the deficiencies associated with the insurance claim and thereby re-billing the insurance claim. The program may further include programmed instructions for confirming and validating the processing of the insurance claim associated with the patient and posting the insurance claim for payment to the payor. Further, the program may include programmed instructions for displaying, on a user device associated with the physician, the entire RCM workflow and a financial status, and further one or more of the transcription template populated with the one or more data fields, a charge entry form populated with the one or more codes to be submitted to a clearing house or the payor, and an indicative amount to be paid by the payor, wherein the indicative amount is populated and displayed based upon the data from the transcription template and the charge entry form. Furthermore, the program may include programmed instructions for continuously training the program based upon historical data associated with transcription, coding, billing, over-payment, under-payment, or denial of prior insurance claims.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings to refer to like features and components.

DETAILED DESCRIPTION

Some embodiments of this disclosure, illustrating all its features, will now be discussed in detail. The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that, the singular forms "a," "an," and "the" include plural references unless the context clearly dictates otherwise. Although any methods similar or equivalent to those described herein can be used in the practice or testing of embodiments of the present disclosure, the exemplary methods are now described. The disclosed embodiments are merely exemplary of the disclosure, which may be embodied in various forms.

Various modifications to the embodiment will be readily apparent to those skilled in the art and the generic principles herein may be applied to other embodiments. However, one of ordinary skill in the art will readily recognize that the present disclosure is not intended to be limited to the embodiments illustrated, but is to be accorded the widest scope consistent with the principles and features described herein.

While aspects of the described system and method of facilitating revenue cycle management in healthcare may be implemented in any number of different computing systems, environments, and/or configurations, the embodiments may be described in the context of the following exemplary system.

Figure 1:
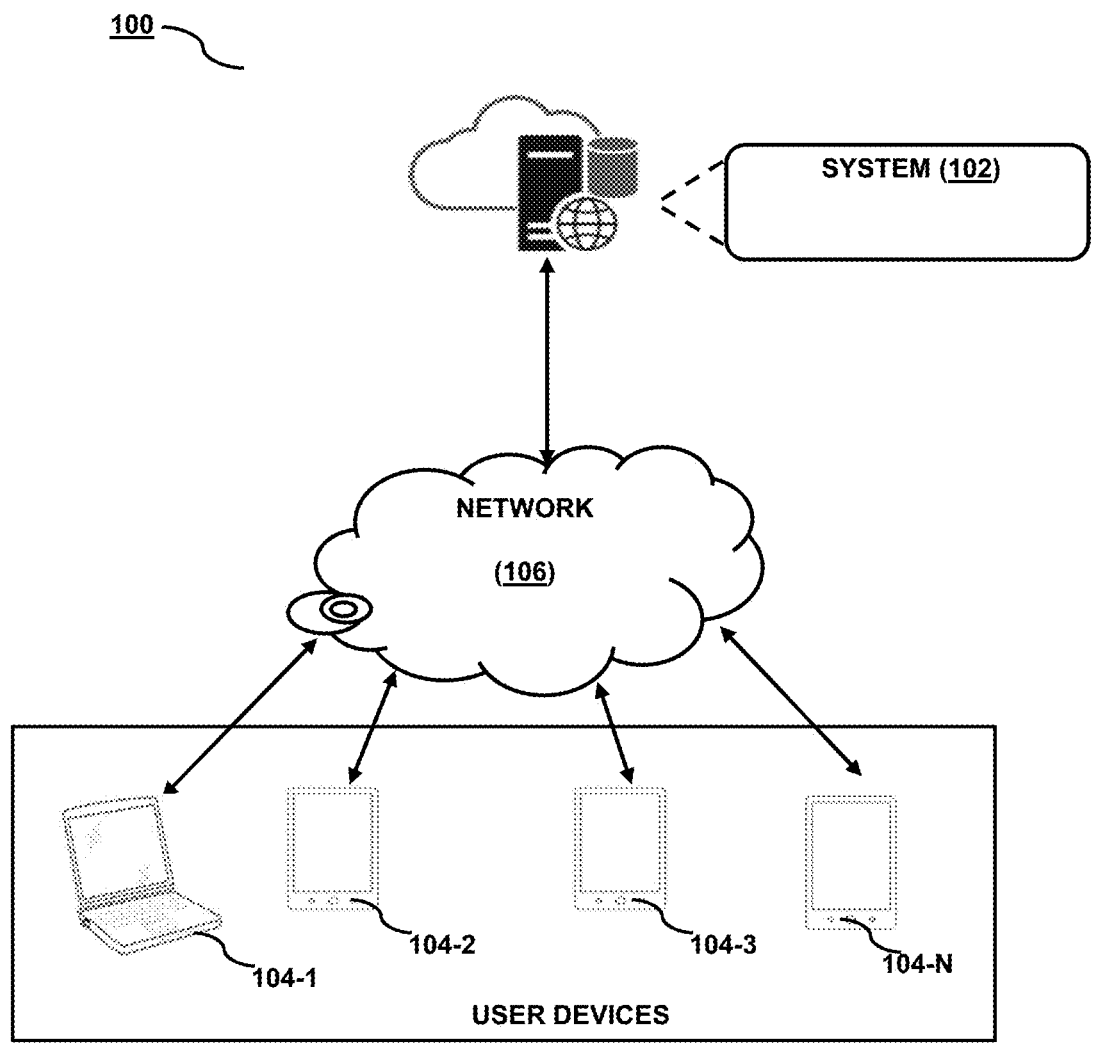
FIG. 1 is a diagram of a network implementation of a system of facilitating revenue cycle management in healthcare, in accordance with an embodiment of the present disclosure.

Referring now to FIG. 1, a network implementation 100 of a system 102 of facilitating revenue cycle management in healthcare is shown, in accordance with an embodiment of the present subject matter. Although the present subject matter is explained considering that the system 102 is implemented on a server, it may be understood that the system 102 may also be implemented in a variety of computing systems, such as a laptop computer, a desktop computer, a notebook, a workstation, a mainframe computer, a server, a network server, a cloud-based computing environment and the like. In one implementation, the system 102 may be implemented in a cloud-based computing environment. It will be understood that the system 102 also may be accessed by multiple registered users through one or more user devices 104-1, 104-2, 104-3, or 104-N. Examples of the user devices 104 may include, and are not limited to, a portable computer, a personal digital assistant, a handheld device, and a workstation. Further, the system 102 may be communicatively coupled with the user devices 104-1, 104-2, 104-3, or 104-N, through a network 106.

In one implementation, the network 106 may be a wireless network, a wired network or a combination thereof. The network 106 can be implemented as one of the different types of networks, such as intranet, local area network (LAN), wide area network (WAN), the internet, and the like. The network 106 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), a telecommunication network (e.g. 2G/3G/4G/5G) and the like, to communicate with one another. Further the network 106 may include a variety of network devices, including routers, bridges, servers, computing devices, storage devices, and the like.

Figure 2:
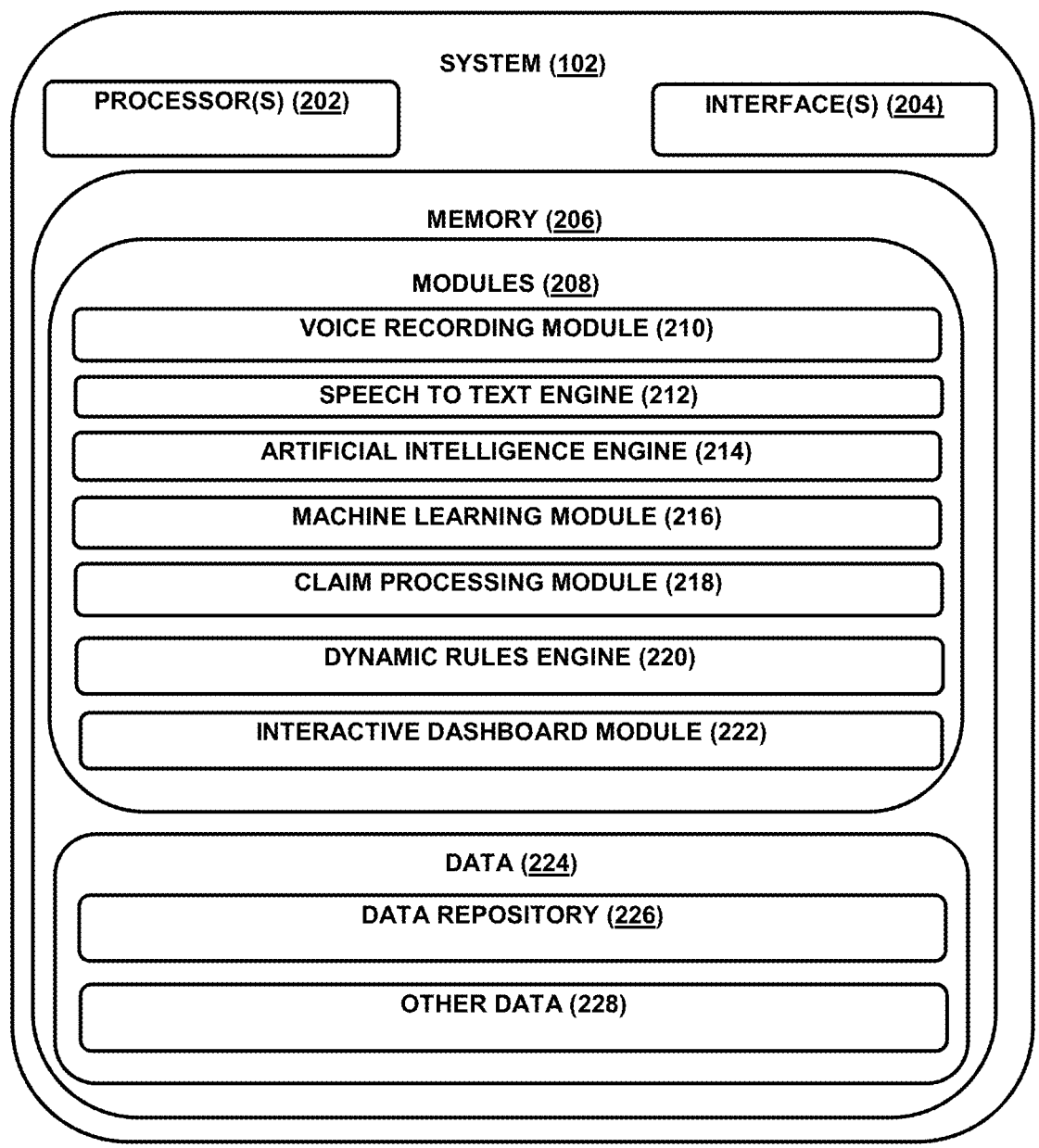
FIG. 2 is a diagram of the system, in accordance with an embodiment of the present disclosure.

Referring now to FIG. 2, the system 102 is illustrated in accordance with an embodiment of the present disclosure. In one embodiment, the system 102 may include a processor 202, an input/output (I/O) interface 204, and a memory 206. The processor 202 may be implemented as one or more microprocessors, microcomputers, microcontrollers, digital signal processors, central processing units, state machines, logic circuitries, and/or any devices that manipulate signals based on operational instructions. Among other capabilities, the processor 202 is configured to fetch and execute computer-readable instructions stored in the memory 206.

The I/O interface 204 may include a variety of software and hardware interfaces, for example, a web interface, a graphical user interface, and the like. The I/O interface 204 may allow the system 102 to interact with the user/consumer directly or through the consumer devices 104. Further, the I/O interface 204 may enable the system 102 to communicate with other computing devices, such as web servers and external data servers (not shown). The I/O interface 204 can facilitate multiple communications within a wide variety of networks and protocol types, including wired networks, for example, LAN, cable, etc., and wireless networks, such as WLAN, cellular, or satellite. The I/O interface 204 may include one or more ports for connecting a number of devices to one another or to another server.

The memory 206 may include any computer-readable medium and computer program product known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The memory 206 may include modules 208 and data 224.

The modules 208 include routines, programs, objects, components, data structures, etc., which perform particular tasks or implement particular abstract data types. In one implementation, the modules 208 may include a voice recording module 210, a speech to text engine 212, an artificial intelligence engine 214, a machine learning module 216, a claim processing module 218, dynamic rules engine 220, an interactive dashboard module 222, and other modules (not shown). The other modules may include programs or coded instructions that supplement applications and functions of the system 102.

The data 224, amongst other things, serves as a repository for storing data processed, received, and generated by one or more of the modules 208. The data 224 may also include a data repository 226 and other data 228. The other data 228 may include data generated as a result of the execution of one or more modules in the other modules. The system 102 may be accessed by the user device 104 registered with the system 102. The user device 104 may belong to a physician or a doctor. Further, each of the aforementioned modules is explained in subsequent paragraphs of the specification.

Now referring to FIG. 2, the voice recording module 210 may record a voice or an audio of a physician or a doctor (hereafter referred as physician) treating a patient. The physician or the doctor may dictate a diagnosis or a treatment via the user device 104. The diagnosis and treatment dictated by the physician may be recorded by the voice recording module 210. The voice or audio recorded by the voice recording module 210 may be stored in the data repository 226.

Based upon the recording of the voice of the physician, the speech to text engine 212, as shown in FIG. 2, may be configured to covert the voice into text format. A person skilled in the art would easily realize and appreciate that the speech to text engine 212 may use advanced deep learning functionalities of automatic speech recognition (ASR) technologies for converting speech to text format. Specifically, the speech to text engine 212 may convert voice/audio associated with each of the diagnosis and treatment into textual format to generate a transcription file. For the purposes of this disclosure, a transcription file is a textual file capturing the treatment, diagnosis or consultation given to the patient by the physician. Further, as shown in FIG. 2, the artificial intelligence engine 214 may be configured to automatically correct the textual data in the transcription file. It must be understood that the artificial intelligence engine 214 may be adaptively trained via the machine learning module 216 to rectify the errors in the textual data in the transcription file. The transcription file corrected may be stored in the data repository 226.

Figure 3A:
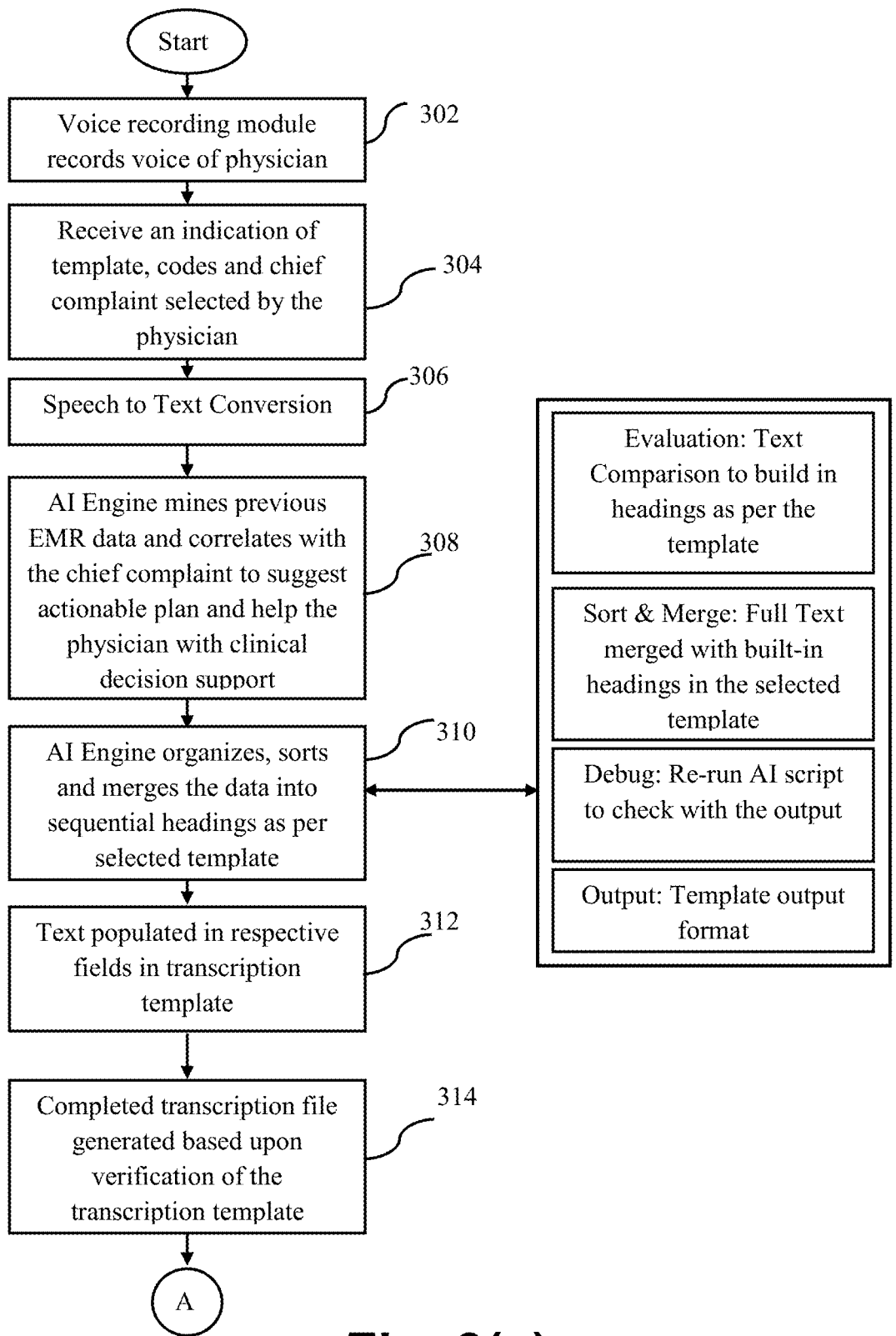
FIG. 3(a), FIG. 3(b), FIG. 3(c) and FIG. 3(d) are flow diagrams depicting working of an artificial intelligence engine and a claim processing module within the system 102, in accordance with an embodiment of the present disclosure.

In one embodiment, as shown in FIG. 2, the artificial intelligence engine 214 may be configured to process the textual data in the transcription file. The artificial intelligence engine 214 may be configured to process the text in order to automatically populate one or more data fields in a template selected from a plurality of predefined templates stored in the data repository 226. Each template of the plurality of templates is associated with different stages of the diagnosis and treatment of the patients. For example, the template may be associated with initial consultation, diagnosis detected, treatments suggested, or discharge summary. For each different template, different data fields may be required to be populated in the respective template. In one embodiment, each predefined template may indicate an electronic medical record (EMR) or electronic health record (EHR) for the patient being treated by the physician. In one embodiment, the one or more data fields in the predefined template may include vitals, diagnosis, and treatment etc. The rules from the dynamic rules engine 220 which sets the rules based on the outcome/learning of the artificial intelligence engine 214 automatically populates the one or more fields with corresponding text from the transcription file. In one embodiment, a data field "vitals" may be populated with blood pressure, temperature, etc. Further, a data field "diagnosis" may be populated with text corresponding to the diagnosis dictated by the physician. A person skilled in the art would easily realize and appreciate that the artificial intelligence engine 214 may populate the one or more data fields with the text in the transcription file using text processing techniques such as Natural Language Processing (NLP), semantic and/or syntactic analysis, and the like. FIG. 3(a) illustrates a method implemented by the artificial intelligence engine 214 for automatically populating the one or more data fields in the template selected from the plurality of predefined templates stored in the data repository 226.

As shown in FIG. 3(a), at step 302, the voice recording module 210 may record a voice dictated by the physician. At step 304, an indication of a template, one or more codes, and chief complaint selected by the physician via the user device associated with the physician may be received by the system. At step 306, the speech is converted into a text format via the speech to text engine 212. At step 308, the artificial engine mines previous EMR data and correlates the previous EMR data with the chief complaint to suggest an actionable plan to the physician/doctor and help the physician/doctor with the clinical decision support. At step 310, the artificial intelligence engine 214 organizes sorts and merges the data from the text into sequential headings as per the template selected from the plurality of predefined templates. Specifically, at step 310, the artificial intelligence engine 214 compares the text in the transcription file to the built-in headings in the template selected. In one example, the name of the patient may be populated in the "Patient Name" column, chief complaint of the patient may be populated in the "Chief Complaint" heading etc. as per the template selected. Further, the artificial intelligence engine 214 merges the full text with the built-in headings as per the template selected. Specifically, after all the headings in the template are populated with the respective text, the artificial intelligence engine 214 merges them in the form of a single clinical document. A script (programmed instructions) associated with the artificial intelligence engine 214 is re-run to check with the output. Finally, at the end of step 310, template output format is obtained. At step 312, the artificial intelligence engine 214 automatically populates the respective fields in the transcription template (i.e. the template output format). At step 314, a completed transcription file based upon verification of the transcription template by the transcription quality assurance (QA) team may be generated. The machine learning module 216 may monitor the changes made in the completed transcription file as compared to the transcription template and train the artificial intelligence engine 214 to adapt the changes made in the transcription template.

Figure 3B:
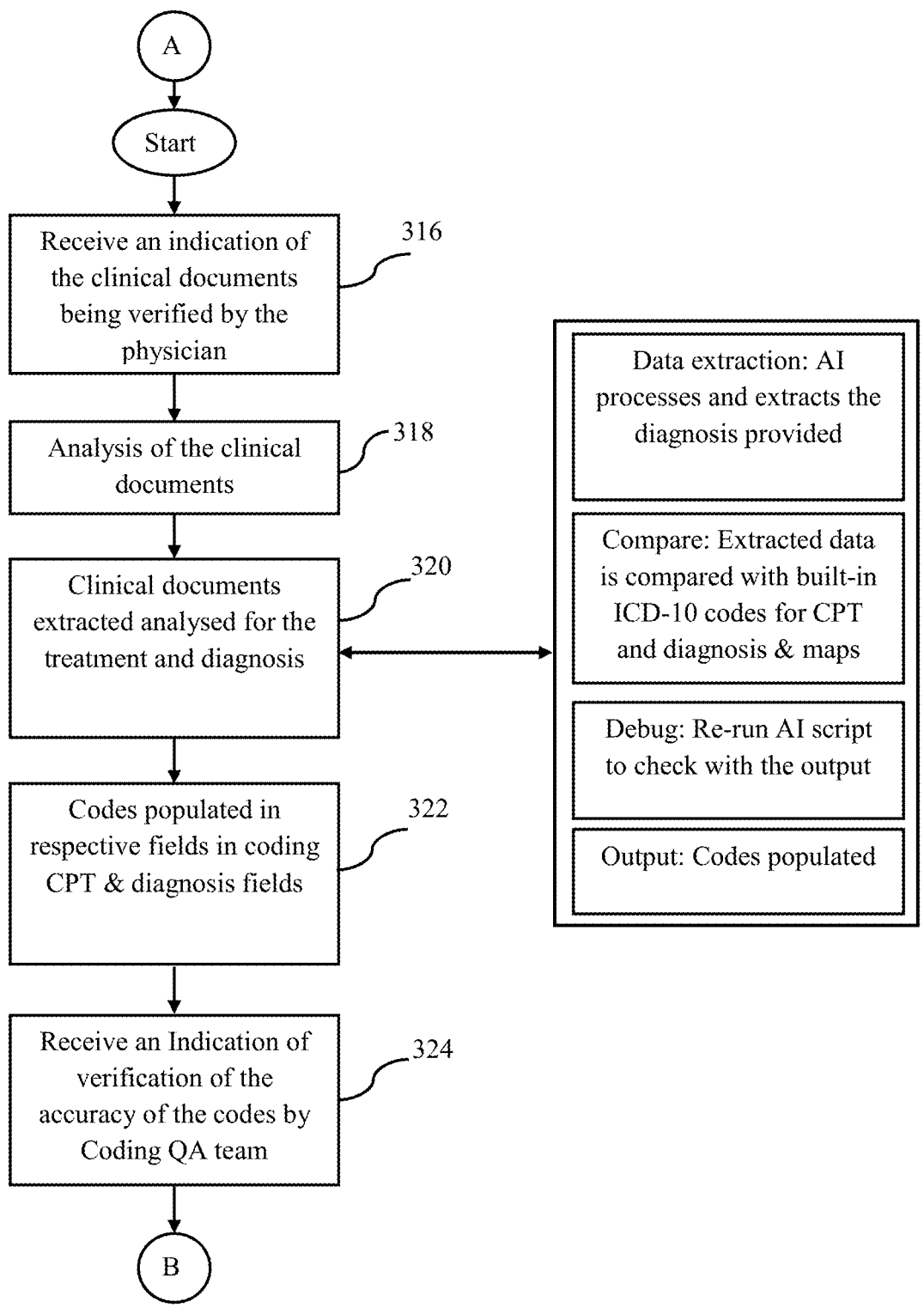

Now referring to FIG. 2, the artificial intelligence engine 214 may process the one or more documents (including the clinical document) associated with the diagnosis and treatment of the patient in order to identify one or more codes from a plurality of codes within an ICD library stored in the data repository 226. Each code of the plurality of codes is associated with a specific diagnosis and specific treatment and further having an associated appropriate monetary amount. The one or more codes identified may be populated in one or more coding fields. FIG. 3(b) illustrates a method implemented by the artificial intelligence engine 214 for automatically populating the one or more coding fields in the transcription template.

As shown in FIG. 3(b), at step 316, an indication of the clinical documents associated with the consultation, diagnosis and treatment for the patient being verified by physician may be received by the system. At step 318, analysis of the clinical documents is initiated. At step 320, the clinical documents are analyzed for the treatment and diagnosis. Specifically, the artificial intelligence engine 214 processes the clinical documents and extracts data associated with the diagnosis provided. The data extracted is compared with built-in ICD-10 codes for (Current Procedural Terminology) CPT and diagnosis and mapping the data with one or more ICD-10 codes. A script (programmed instructions) associated with the artificial intelligence engine 214 is re-run to check with the output. Finally, at the end of step 320, codes mapped are obtained as an output. At step 322, the codes mapped are automatically populated in respective fields in coding CPT & diagnosis fields. At step 324, an indication of the accuracy of the codes mapped being verified by a coding quality assurance (QA) team may be received by the system. The machine learning module 216 may monitor the changes made in the coding fields based upon the verification of the accuracy of the codes and train the artificial intelligence engine 214 to adapt the changes made in the coding fields.

Figure 3C:
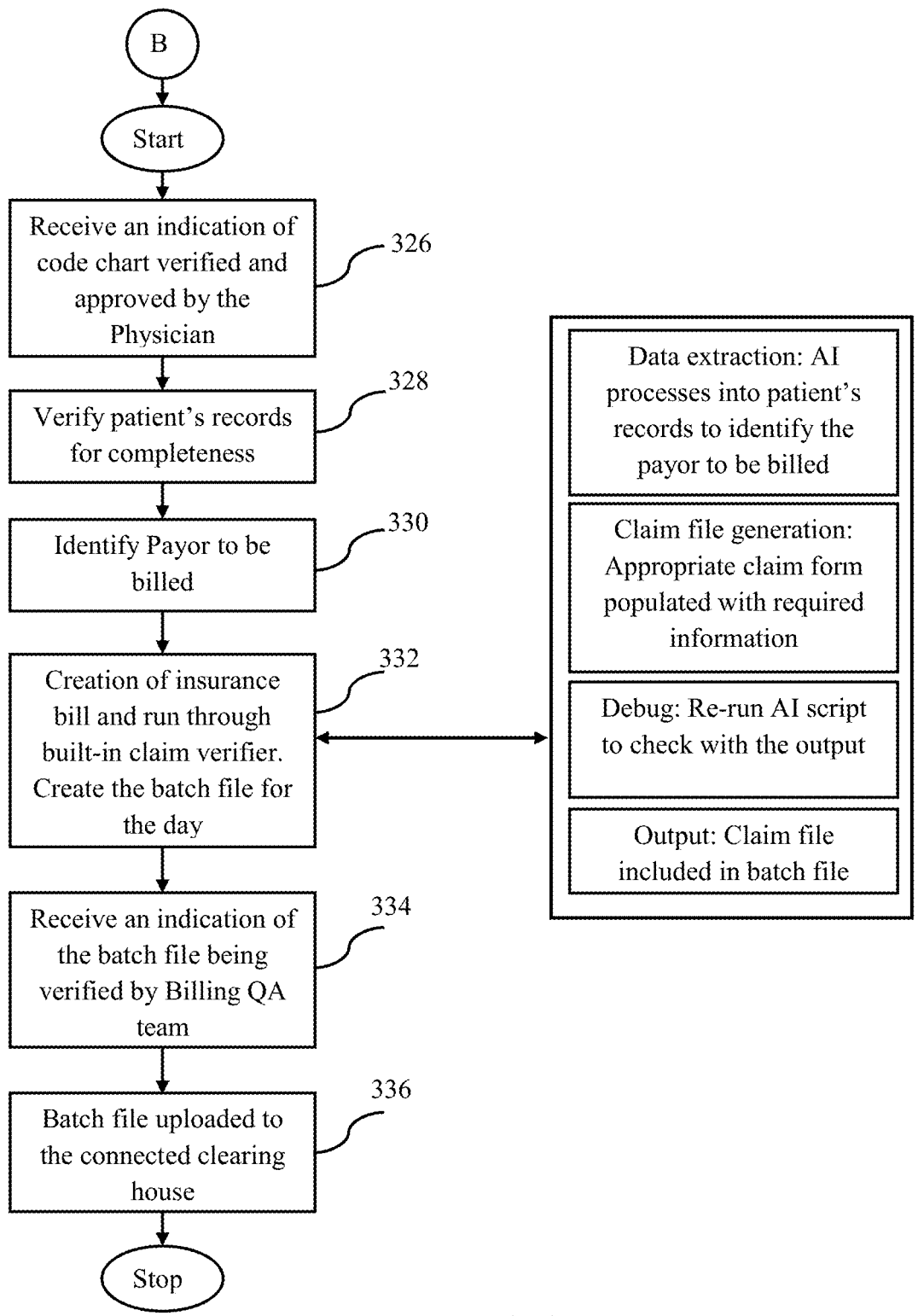

Now again referring to FIG. 2, the artificial intelligence engine 214 may further process data records associated with the patient to automatically populate one or more fields in an insurance claim form of an insurance claim associated with the patient and identify a payor to be billed with an appropriate amount determined based upon the one or more codes identified. FIG. 3(c) illustrates a method implemented by the artificial intelligence engine 214 for automatically populating the one or more fields in the insurance claim form associated with the patient and to identify the payor for processing the appropriate insured amount.

As shown in FIG. 3(c), at step 326, an indication of the code chart, depicting the codes mapped with the treatment and diagnosis of the patient, being verified and approved by the physician may be received in the system. At step 328, the patient's records are verified by the system for completeness of the patient's records. At step 330, a payor to be billed is identified. At step 332, an insurance bill is created and run through the built-in claim verifier. A batch file is generated for the day. In the process of creating the insurance bill, the artificial intelligence engine 214 may process the patient's records to identify the payor to be billed. Further, the artificial intelligence engine 214 processes the patient's records to automatically populate the one or more fields in the insurance claim form with required information. A script (programmed instructions) associated with the artificial intelligence engine 214 is re-run to check with the output. Finally, at the end of step 332, a claim file is obtained as an output and included in the batch file. At step 334, an indication of the batch file being verified by a billing quality assurance (QA) team may be received in the system. The machine learning module 216 may monitor the changes made by the billing QA team in the batch file based upon the verification of the batch file and train the artificial intelligence engine 214 to adapt the changes made in the batch file. At step 336, the batch file is uploaded to a connected clearing house for processing the insurance amount claimed.

Figure 3D:
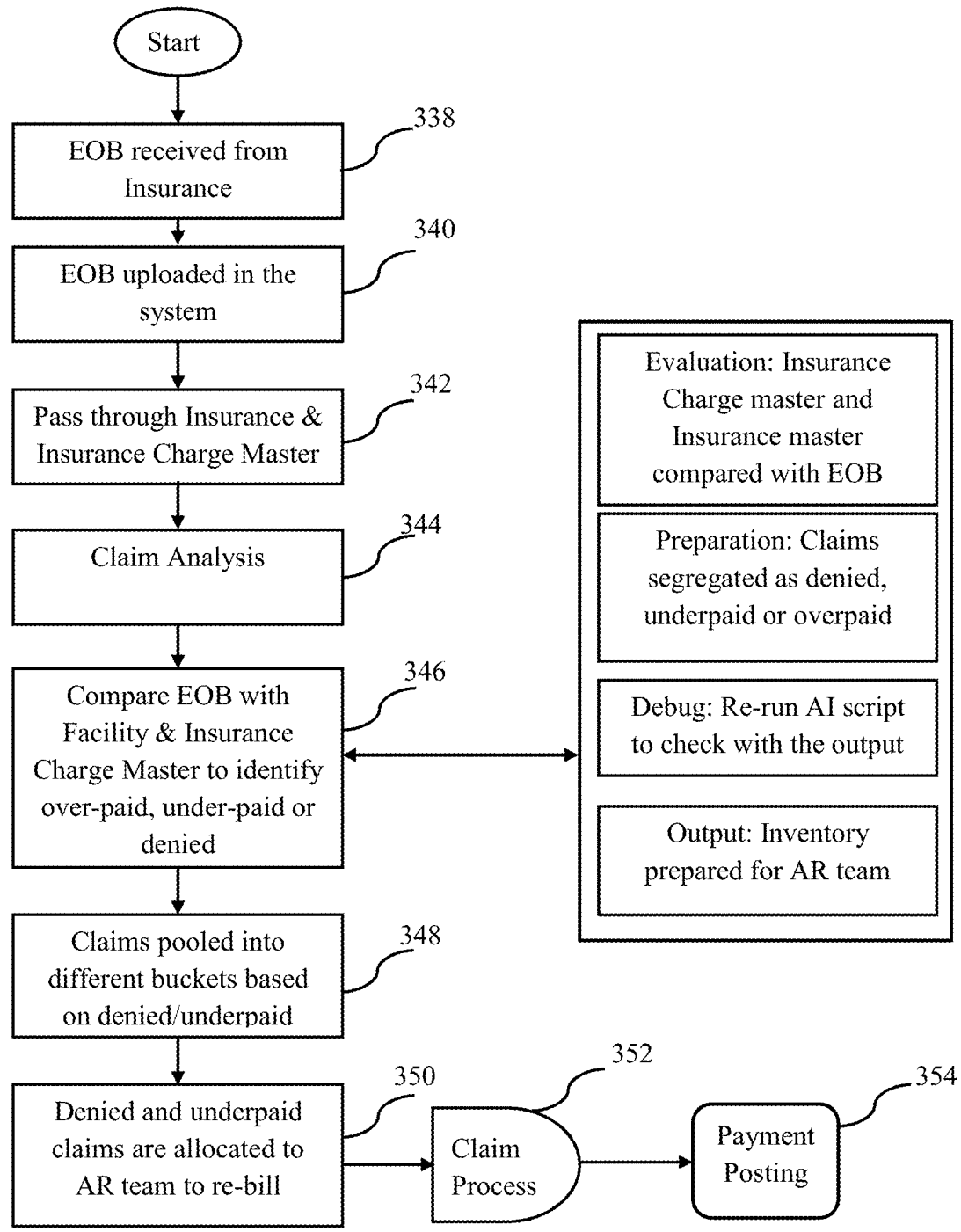

Now again referring to FIG. 2, the artificial intelligence engine 214 may further compare explanation of benefits (EOB) associated to the insurance claim with a predefined master file to detect the insurance claim being underpaid, overpaid, or denied. The master file may include a fee schedule available for the insurance claims. In one embodiment, the master file includes fees that facilities may normally charge for a particular treatment or diagnosis and a standard fee schedule received from multiple insurance companies. FIG. 3(d) illustrates a method implemented collectively by the artificial intelligence engine 214 and the claim processing module 218 for comparing explanation of benefits (EOB) associated to the insurance claim with the predefined master file to detect the insurance claim being underpaid, overpaid, or denied and thereby process the claim accordingly.

As shown in FIG. 3(d), at step 338, the EOB may be received from the Insurance team. At step 340, the EOB may be uploaded in the system 102. At step 342, the EOB may be passed through the insurance charge master and insurance master (i.e. the master file) stored in the data repository 226. At step 344, the claim received may be subjected to analysis. At step 346, the EOB may be compared with the insurance charge master and insurance master in order to identify whether the insurance claim is over-paid, under-paid or denied. The analysis at step 346 may include comparing the insurance charge master and the insurance master with the EOB. The analysis at step 346 may further include segregating the insurance claim into either denied, underpaid, or overpaid. A script (programmed instructions) associated with the artificial intelligence engine 214 is re-run to check with the output. Finally, at the end of step 346, an inventory associated with the insurance claim is prepared and sent to the Accounts Receivable (AR) team. At step 348, the insurance claim if detected as denied/underpaid may be pooled into denied or underpaid buckets. At step 350, the denied/underpaid claim may be re-assessed by the artificial intelligence engine 214 to correct the deficiencies and/or incorrect information associated with the insurance claim and thereby re-bills the insurance claim. In some embodiments, the insurance claim may be allocated to the Accounts Receivable (AR) team to manually connect with the insurance company in order to follow-up/adjudicate/re-bill. The AR/billing team may reassess the insurance claim and thereby correct the deficiencies associated with the insurance claim. At step 352, based upon the adjudication or re-billing of the insurance claim, the claim processing module 218 may confirm and validate the processing of the insurance claim associated with the patient. Further, at step 354, the insurance claim for payment may be posted to the payor.

Figure 4:
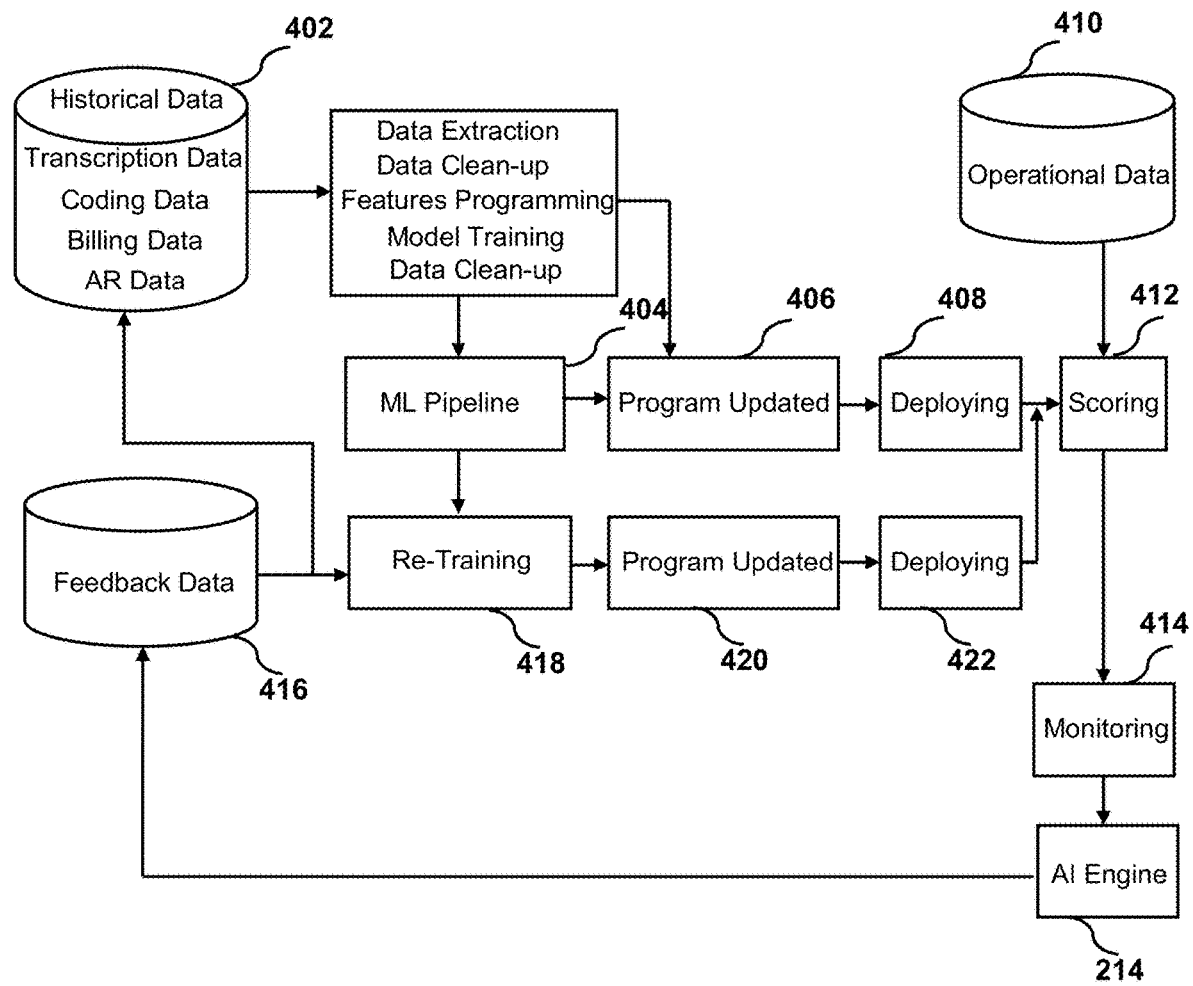
FIG. 4 is a flow diagram depicting working of a machine learning module within the system 102, in accordance with an embodiment of the present disclosure.

As explained above, the outputs of each of the aforementioned steps, performed by the artificial intelligence engine 214, including the transcription template, the codes mapped, claim insurance form and the claim processing may be changed and/or rectified via manual interventions. These changes may be monitored by the machine learning module 216 and accordingly train the artificial intelligence engine 214 to adapt with these changes for determining error-free outputs in future. Referring to FIG. 4 is a flow diagram depicting working of a machine learning module 216 within the system 102, in accordance with an embodiment of the present disclosure.

As shown in FIG. 4, at step 402 and step 416, the historical data that includes the existing Transcription, Coding, Billing and AR information available in the system along with Feedback data received from the Artificial Intelligence (AI) engine 214 is taken into consideration to analyze and re-train the system at step 418. The system achieves this process by creating a Machine Learning (ML) Pipeline at step 404 which is build by required data extracted and cleaned-up from the Historical data and the Feedback data. Once the data clean-up and re-training is completed; the system uses this data to update the existing program and updates the program accordingly at step 406/420 to fine tune the system. The program is then deployed at step 408/422 into the main program which is then funneled into scoring the results at step 412. Scoring is the process implemented to ensure the re-programming performed from data used by the historical data, the feedback data and day to day operational data 410 related to transcription, coding, billing and AR is able to achieve better results. The system continuously monitors at step 414 the data and its performance in a live environment. Further to this, the results derived from the monitoring step is then passed back to the AI engine 214, which further feeds into the feedback data and the cycle continues.

Figure 5A:
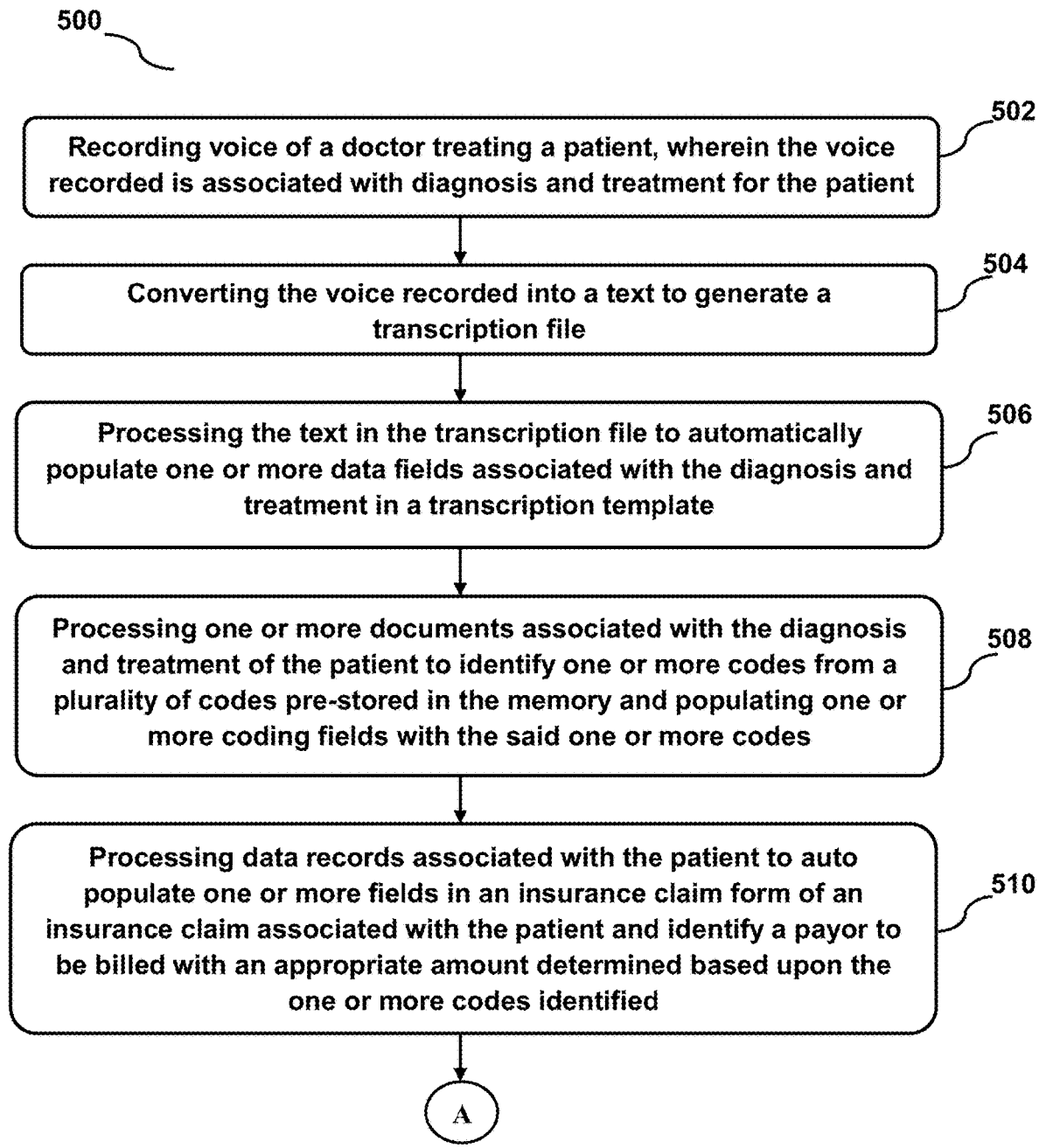
FIG. 5(a) and FIG. 5(b) are flow diagrams depicting a method of facilitating revenue cycle management in healthcare, in accordance with an embodiment of the present disclosure.
Figure 5B:
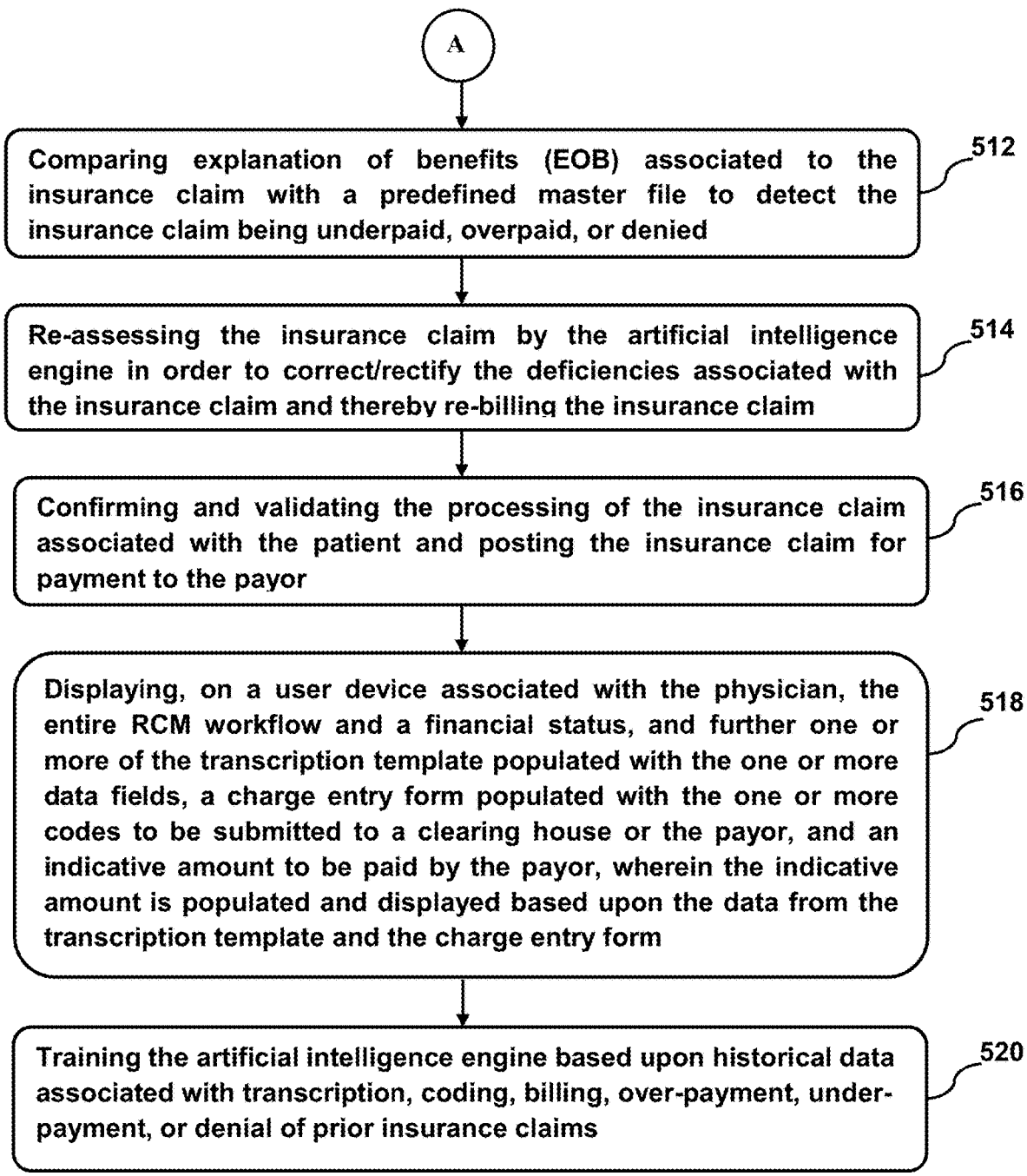

Now referring to FIG. 5(a) and FIG. 5(b), a method 500 of facilitating revenue cycle management in healthcare is shown, in accordance with an embodiment of the present subject matter. The method 500 may be described in the general context of computer executable instructions. Generally, computer executable instructions can include routines, programs, objects, components, data structures, procedures, modules, functions, etc., that perform particular functions or implement particular abstract data types. The method 500 may also be practiced in a distributed computing environment where functions are performed by remote processing devices that are linked through a communications network. In a distributed computing environment, computer executable instructions may be located in both local and remote computer storage media, including memory storage devices.

The order in which the method 500 is described is not intended to be construed as a limitation, and any number of the described method blocks can be combined in any order to implement the method 500 or alternate methods. Additionally, individual blocks may be deleted from the method 500 without departing from the spirit and scope of the disclosure described herein. Furthermore, the method can be implemented in any suitable hardware, software, firmware, or combination thereof. However, for ease of explanation, in the embodiments described below, the method 500 may be considered to be implemented in the above described in the system 102.

At block 502, a voice of a physician treating a patient may be recorded. The voice recorded may be associated with a diagnosis and treatment for the patient. In an implementation, the voice of the physician may be recorded via the voice recording module 210 of the system 102.

At block 504, the voice recorded may be converted into a text format to generate a transcription file. In an implementation, the voice may be converted into the text format via the speech to text engine 212 of the system 102.

At block 506, the text in the transcription file may be processed to automatically populate one or more data fields associated with the diagnosis and treatment in a transcription template. In an implementation, the text in the transcription file may be processed via the artificial intelligence engine 214 of the system 102.

At block 508, one or more documents associated with the diagnosis and treatment of the patient may be processed to identify one or more codes from a plurality of codes pre-stored in the memory and populating one or more coding fields with the said one or more codes. In an implementation, the one or more documents associated with the diagnosis and treatment of the patient may be processed via the artificial intelligence engine 214 of the system 102.

At block 510, data records associated with the patient may be processed to automatically populate one or more fields in an insurance claim form of an insurance claim associated with the patient and identify a payor to be billed with an appropriate amount determined based upon the one or more codes identified. In an implementation, the data records associated with the patient may be processed via the artificial intelligence engine 214 of the system 102.

At block 512, explanation of benefits (EOB) associated to the insurance claim may be compared with a predefined master file to detect the insurance claim being underpaid, overpaid, or denied. In an implementation, the EOB may be compared with the predefined master file via the artificial intelligence engine 214 of the system 102.

At block 514, the insurance claim being detected as underpaid, overpaid, or denied may be reassessed by the artificial intelligence engine 214 in order to correct/rectify the deficiencies associated with the insurance claim and thereby re-billing the insurance claim. In an alternative embodiment, the insurance claim may be allocated to the Accounts Receivable (AR) team to manually connect with the insurance company in order to follow-up/adjudicate/re-bill.

At block 516, the processing of the insurance claim associated with the patient may be confirmed, validated and posted for payment to the payor. In an implementation, the insurance claim insurance claim associated with the patient may be confirmed, validated and posted for payment to the payor via the claim processing module 218 of the system 102.

At block 518, the interactive dashboard module 222 of the system 102 may display, on a user device associated with the physician, the entire RCM workflow and a financial status, and further one or more of the transcription template populated with the one or more data fields, a charge entry form populated with the one or more codes to be submitted to a clearing house or the payor, and an indicative amount to be paid by the payor. In accordance with aspects of the disclosure, the indicative amount may be populated and displayed based upon the data from the transcription template and the charge entry form. It must be understood that the financial status herein includes the current status/stage of the claim. Further, the charge entry form includes the one or more codes added in the medical coding stage which is further populated in the insurance claim form (i.e. the information to be populated to electronically submit the claim).

At block 520, the artificial intelligence engine 214 may be trained based upon historical data associated with transcription, coding, billing, over-payment, under-payment, or denial of prior insurance claims. In an implementation, the artificial intelligence engine 214 may be trained via the machine learning module 216 of the system 102.

Although implementations for method(s) and system(s) of facilitating revenue cycle management in healthcare have been described in language specific to structural features and/or methods, it is to be understood that the implementations and/or embodiments are not necessarily limited to the specific features or methods described. Rather, the specific features and methods are disclosed as examples of implementations for method and system of facilitating revenue cycle management in healthcare.

What is claimed is:

1. A computer implemented system, the system comprising:
   a hardware processor; and
   a memory coupled with the hardware processor, wherein the hardware processor executes a plurality of modules stored in the memory, the plurality of modules comprising:
      a voice recording module, via the hardware processor, configured to receive a voice of a physician treating a patient from a computing device over a network and record said voice of the physician treating the patient, wherein the voice recorded is associated with a diagnosis and treatment for the patient;
      a speech to text engine, via the hardware processor, configured to convert the voice recorded into a text format to generate a transcription file, wherein an artificial intelligence engine mines previous electronic medical record (EMR) data with complaint identified with the diagnosis to indicate said treatment to the physician for clinical decision support;
      a dynamic rules engine, via the hardware processor, configured to execute in tandem with the artificial intelligence engine to process and analyze the text in the transcription file to automatically populate one or more data fields associated with the diagnosis and treatment in a transcription template, said transcription template being selected from a plurality of predefined templates based on a predefined set of rules, each of the plurality of predefined templates being associated with different stages of diagnosis;
wherein the modules are configured to cause the hardware processor to:
process, via the hardware processor, one or more documents associated with the diagnosis and treatment of the patient to provide clinical decision support, and identify, via the hardware processor, one or more codes from a plurality of codes pre-stored in the memory to populate one or more coding fields of the selected transcription template with the one or more codes, each of the plurality of codes being associated with a particular treatment and corresponding treatment value, wherein the artificial intelligence engine is configured to process the transcription file and one or more documents associated with the treatment and diagnosis by:
extracting data from the one or more documents;
processing and comparing the extracted data with the plurality of codes pre-stored in the memory; and
mapping the extracted data with the one or more codes selected from the plurality of codes, wherein the plurality of codes pre-stored in the memory is built-in International classification diseases (ICD) codes for current procedural terminology;
identify, via the hardware processor, a payor to be billed with an amount determined based upon the one or more codes; and
output, via the hardware processor, a batch file based on processing of the selected transcription template, the payor, and the amount, wherein the output batch file is verifiable and a machine learning module monitors changes made to said output batch file post verification of the output batch file so as to train the artificial intelligence engine to adapt with the changes made in the output batch file.

2. The system of claim 1, wherein the artificial intelligence engine is configured to auto-correct the text obtained from the speech to text engine based upon an input received from a machine learning module.

3. The system of claim 2, wherein the artificial intelligence engine is configured to process the text in the transcription file by organizing, sorting, and merging textual data in the transcription file into sequential headings as per the transcription template selected.

4. The system of claim 1, wherein each code of the plurality of codes is mapped with a predetermined insurance amount to be billed and forwarded to the payor.

5. The system of claim 1, wherein the artificial intelligence engine is further configured to compare explanation of benefits (EOB) associated to an insurance claim associated with the patient with a predefined master file to detect the insurance claim being underpaid, overpaid, or denied.

6. The system of claim 5, wherein the master file comprises a fee schedule available for the insurance claims.

7. The system of claim 6, wherein the insurance claim being detected as underpaid, overpaid, or denied is further reassessed by the artificial intelligence engine in order to correct the deficiencies associated with the insurance claim and thereby re-bill the insurance claim.

8. The system of claim 7, wherein the hardware processor further executes a claim processing module stored in the memory to confirm and validate the processing of the insurance claim associated with the patient and posting the insurance claim for payment to the payor.

9. The system of claim 8, further comprising a machine learning module for continuously training the artificial intelligence engine based upon historical data associated with transcription, coding, billing, over-payment, under-payment, or denial of prior insurance claims.

10. A computer implemented method, the method comprising:
receiving a voice of a physician treating a patient from a computing device over a network and recording, via a hardware processor, said voice of the physician treating the patient, wherein the voice recorded is associated with a diagnosis and treatment for the patient;
converting, via the hardware processor, the voice recorded into a text format to generate a transcription file, wherein an artificial intelligence engine mines previous electronic medical record (EMR) data with complaint identified with the diagnosis to indicate said treatment to the physician for clinical decision support;
processing, via the hardware processor, the text in the transcription file to automatically populate one or more data fields associated with the diagnosis and treatment in a transcription template selected from a plurality of predefined templates based on a predefined set of rules, each of the plurality of predefined templates being associated with different stages of diagnosis;
processing, via the hardware processor, one or more documents associated with the diagnosis and treatment of the patient to identify one or more codes from a plurality of codes pre-stored in memory and populating one or more coding fields of the selected transcription template with the said one or more codes, each of the plurality of codes being associated with a particular treatment and corresponding treatment value, wherein processing the one or more documents comprises:
extracting data from the one or more documents;
processing and comparing the extracted data with the plurality of codes pre-stored in the memory; and
mapping the extracted data with the one or more codes selected from the plurality of codes, wherein the plurality of codes pre-stored in the memory is built-in International classification diseases (ICD) codes for current procedural terminology;
identifying, via the hardware processor, a payor to be billed with an amount determined based upon the one or more codes; and
outputting, via the hardware processor, a batch file based on processing of the selected transcription template the payor, and the amount, wherein the output batch file is verifiable and a machine learning module monitors changes made to said output batch file post verification of the output batch file so as to train the artificial intelligence engine to adapt with the changes made in the output batch file.

* * * * *